US008569305B2

(12) United States Patent
Arbiser

(10) Patent No.: US 8,569,305 B2
(45) Date of Patent: Oct. 29, 2013

(54) TREATMENT OF TUBEROUS SCLEROSIS ASSOCIATED NEOPLASMS

(75) Inventor: Jack Arbiser, Atlanta, GA (US)

(73) Assignee: Emory University, Atlanta, GA (US)

( * ) Notice: Subject to any disclaimer, the term of this patent is extended or adjusted under 35 U.S.C. 154(b) by 501 days.

(21) Appl. No.: 11/603,747

(22) Filed: Nov. 22, 2006

(65) Prior Publication Data

US 2007/0078142 A1   Apr. 5, 2007

Related U.S. Application Data

(63) Continuation of application No. 10/655,407, filed on Sep. 4, 2003, now abandoned.

(60) Provisional application No. 60/408,550, filed on Sep. 5, 2002.

(51) Int. Cl.
*A61K 31/497*   (2006.01)

(52) U.S. Cl.
USPC ..................................... 514/252.18; 544/295

(58) Field of Classification Search
None
See application file for complete search history.

(56) References Cited

U.S. PATENT DOCUMENTS

| 5,521,184 A | 5/1996 | Zimmermann | |
|---|---|---|---|
| 6,380,360 B1 * | 4/2002 | Harris et al. | 530/350 |
| 2003/0124534 A1 * | 7/2003 | Rastelli et al. | 435/6 |
| 2003/0185831 A1 * | 10/2003 | Cutler et al. | 424/155.1 |
| 2005/0209244 A1 * | 9/2005 | Prescott et al. | 514/252.18 |

FOREIGN PATENT DOCUMENTS

| WO | WO 99/03854 | 1/1999 |
|---|---|---|
| WO | WO 02/22597 | 3/2002 |
| WO | WO 02/45652 | 6/2002 |
| WO | WO 02/47690 | 6/2002 |
| WO | WO 03/011836 | 2/2003 |
| WO | WO 03/011837 | 2/2003 |
| WO | WO 03/011838 | 2/2003 |
| WO | WO 03/015788 | 2/2003 |
| WO | WO 03/029248 | 4/2003 |

OTHER PUBLICATIONS

Arbiser et al., "Functional Tyrosine Kinase Inhibitor Profiling", Am. J. Pathol., 161(3), pp. 781-786 (2002; available online Aug. 23, 2002).*
Arbiser et al. "Functional Tyrosine Kinase Inhibitor Profiling", orginial publication date (2002).*
Anonymous. Adult Renal Hamartomas. Archives of RadioGraphics. 1997;17:155-169; electronic pp. 1-5, last updated Feb. 2007.*
Franz et al. Tuberous Sclerosis. http://www.emedicine.com/neuro/TOPIC386.HTM, electronic pp. 1-45, Article last updated Feb. 14, 2007.*
Levitzki. Protein tyrosine kinase inhibitors as novel therapeutic agents. Pharmacol. Ther. 1999; 82(Nos. 2-3): 231-239.*
Arbiser et al., The Journal of Investigative Dermatology, vol. 119, No. 1, p. 208, Abstract #003 (Jul. 2002).
Arbiser J. et al., Functional Tyrosine Kinase Inhibitor Profiling. A Generally Applicable Method Points to a Novel Role of Platelet-Derived Growth Factor Receptor-β in Tuberous Sclerosis, American Journal of Pathology, vol. 161, No. 3, pp. 781-786 (2002.
Exhibit A, email correspondence from USPTO Biotechnology Library confirming date Arbiser et al. article was available to the public, (Mar. 22, 2006).
Goel S. et al., "Tyrosine Kinase Inhibitors: A Clinical Perspective," Current Oncology Reports 2002, 4:9-19 (2002).
Kilic T. et al., "Intracranial Inhibition of Platelet-derived Growth Factor-mediated Glioblastoma Cell Growth by an Orally Active Kinase Inhibitor of the 2-Phenylaminopyrimidine Class," Cancer Research, vol. 60, pp. 5143-5150, (2000).
MedlinePlus Encyclopedia, Tuberous Sclerosis, pp. 1-4 (May 8, 2006).
Radford Ian R., "Imatinib Novartis," Current Opinion in Investigational Drugs, vol. 3(3), pp. 492-499 (2002).
Rubin B. et al., "Molecular Targeting of Platelet-Derived Growth Factor B by Imatinib Mesylate in a Patient With Metastatic Dermatofibrosarcoma Protuberans," Journal of Clinical Oncology, vol. 20, No. 17, pp. 3586-3591 (2002).
Sjöblom T. et al., "Growth Inhibition of Dermatofibrosarcoma Protuberans Tumors by the Platelet-derived Growth Factor Receptor Antagonist STI571 through Induction of Apoptosis," Cancer Research, vol. 61, pp. 5778-5783 (2001).
Spitaler M. et al., "The Involvement of Protein Kinase C Isoenzymes α, ε and ζ in the Sensitivity to Antitumor Treatment and Apoptosis Induction," Anticancer Research, vol. 19, pp. 3969-3976 (1999).

* cited by examiner

*Primary Examiner* — Daniel Sullivan
*Assistant Examiner* — Barbara Frazier
(74) *Attorney, Agent, or Firm* — Emory Patent Group; James C. Mason; Susanne Hollinger

(57) ABSTRACT

The present invention relates to the use of PDGF receptor tyrosine kinase or bcr-abl tyrosine kinase inhibitors, especially of N-phenyl-2-pyrimidine-amine derivatives of formula I,

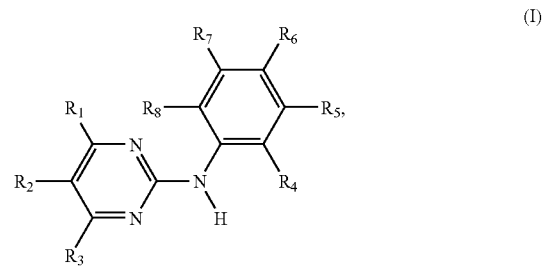

(I)

in which the symbols and substituents have the meaning as defined herein in free form or in pharmaceutically acceptable salt form, in the manufacture of a pharmaceutical composition for the treatment of tuberous sclerosis associated neoplasms; to a method of treatment of warm-blooded animals, including humans, suffering from a tuberous sclerosis associated neoplasms.

5 Claims, No Drawings

TREATMENT OF TUBEROUS SCLEROSIS ASSOCIATED NEOPLASMS

This application is a continuation of U.S. patent application Ser. No. 10/655,407, which claims benefit of U.S. Provisional Application No. 60/408,550, filed Sep. 5, 2002.

The present invention relates to a new use of PDGF receptor tyrosine kinase inhibitors or bcr-abl receptor tyrosine kinase inhibitors, especially of N-phenyl-2-pyrimidine-amine derivatives of formula I (hereinafter: "COMPOUNDS of formula I") in which the symbols and substituents have the meaning as given hereinafter in free form or in pharmaceutically acceptable salt form, in the manufacture of a pharmaceutical composition for the treatment of tuberous sclerosis associated neoplasms, and to a method of treatment of warm-blooded animals, including humans, in which a therapeutically effective dose of a PDGF receptor tyrosine kinase or bcr-abl receptor tyrosine kinase inhibitor is administered to a warm-blooded animal suffering from tuberous sclerosis associated neoplasms.

Tuberous sclerosis (TSC) is an autosomal dominant disorder, with variable penetrance and a frequency in the general population of 1 in 6,000 to 1 in 10,000. The disease is characterized by the development of hamartomas and focal dysplasias in multiple organs including the brain (cortical and subcortical tubers, subependymal nodules, and giant cell astrocytomas, cerebral atrophy, cerebral infarct, cerebral aneurysm, arachnoid cyst), kidney (angiomyolipomas, cysts, carcinomas), skin (hypomelanotic macules, shagreen patches, facial angiofibromas, periungual fibromas), eye (retinal hamartomas), heart (rhabdomyomas), lungs (lymphangioleiomyomatosis), musculoskeletal manifestations (Sclerotic lesions, bone lucencies) and, to a lesser extent, other organs (K. S. Caldemeyer, et al; Tuberous sclerosis—Part I and Part II; J. Am. Acad. Dermatol., (2001) Vol. 45, No. 3, p 448-451).

Tuberous sclerosis is a common autosomal dominant disorder, which leads to neoplasms of the kidney, brain, skin, heart and lung in children and adults. It has been demonstrated that benign neoplasms of tuberous sclerosis are highly angiogenic. TSC-associated brain lesions typically include cortical tubers, subependymal nodules and subependymal giant cell astrocytomas. In the brain, a distinct neoplasm arises in a periventricular area and is termed a subependymal giant cell astrocytoma (SEGA). This neoplasm is cytologically bland, but may grow to large sizes and become surgically unresectable. Radiation therapy of SEGA may result in transformation to a high-grade neoplasm. In the kidney and the heart, the most common TSC-associated lesions are angiomyolipomas (a benign neoplasm of adipose tissue (lipoma) in which muscle cells and vascular structures are fairly conspicuous) and rhabdomyomas, respectively, although oncocytomas and renal cell carcinomas are observed with an increased frequency. Finally, tuberous sclerosis manifests with cutaneous neoplasms including angiofibromas and periungual fibromas. Although not life-threatening as are other visceral tumors, these lesions can cause significant disfigurement and can be difficult to treat. Tumors involving the heart and kidneys can severely affect organ function, while brain lesions can result in seizures, mental retardation, hydrocephalus and autism. Cardiac rhabdomyomas (benign neoplasms derived from striated muscle, occurring in the heart in children, probably as a hamartomatous process) occur around birth and usually resolve spontaneously. Angiomyolipomas are uncommon renal tumors, which are a distinct neoplasm of perivascular epithelioid cells, and exhibit phenotypic markers of smooth muscle, fat, and melanocytes. They are found spontaneously in 1 of 1000 humans, and are the most common renal tumor in tuberous sclerosis complex. Multifocal renal lesions are the major cause of morbidity and mortality in adults with tuberous sclerosis, resulting in hemorrhage, renal failure, and occasional malignant transformation. A malignant version of angiomyolipomas occur sporadically in pancreas, omentum, and female genitourinary tissues, and these lesions may demonstrate loss of tuberin. In addition, similar lesions occur in the lungs of young women and are known as lymphangiomyomatosis. Lymphangiomyomatosis is a hormone sensitive neoplasm, and can sometimes be ameliorated with hormonal therapy. However, the primary modality for treatment of TSC is surgical, and effective medical therapies are lacking for TSC neoplasms. Currently, no medical therapy exists for the treatment of angiomyolipomas of the kidney or SEGAs of the brain, and lesions are treated by either resection or, in the case of smaller angiomyolipomas, by embolization.

Pursuing research in this field, the applicant has surprisingly discovered that platelet-derived growth factor receptor (PDGFR) tyrosine kinase inhibitor especially N-phenyl-2-pyrimidine-amine derivatives of formula I such as COMPOUND I, inhibit the growth of human SV7tert angiomyolipoma cells and murine tsc2ang1 cells in vitro. The applicant has further demonstrated that PDGFRβ is functionally active in the above cell lines, and that functional PDGFRβ is present in authentic human angiomyolipoma tissue.

The instant invention is a response to the need for an alternative therapy in the treatment of tuberous sclerosis associated neoplasms.

It has now surprisingly been demonstrated that tuberous sclerosis associated neoplasms can be successfully treated with PDGF receptor tyrosine kinase or bcr-abl tyrosine kinase inhibitors, especially N-phenyl-2-pyrimidine-amine derivatives of formula I, or pharmaceutically acceptable salt thereof.

The present invention thus concerns the use of PDGF receptor tyrosine kinase or bcr-abl tyrosine kinase inhibitors or a pharmaceutically acceptable salt thereof, for the manufacture of a medicament for treating tuberous sclerosis associated neoplasms.

The present invention furthermore concerns the use of PDGF receptor tyrosine kinase or bcr-abl tyrosine kinase inhibitors or a pharmaceutically acceptable salt thereof, for the manufacture of a medicament for the prevention of neoplasms in patients suffering from tuberous sclerosis.

In particular, the present invention relates to a new use of N-phenyl-2-pyrimidine-amine derivatives of formula I (hereinafter: "COMPOUNDS of formula I"),

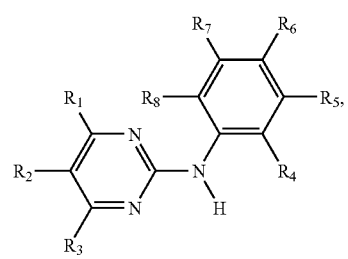

(I)

wherein
$R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl;

one or two of the radicals $R_4$, $R_5$, $R_6$, $R_7$ and $R_8$ are each nitro, fluoro-substituted lower alkoxy or a radical of formula II

  (II), wherein
$R_9$ is hydrogen or lower alkyl,
X is oxo, thio, imino, N-lower alkyl-imino, hydroximino or O-lower alkyl-hydroximino,
Y is oxygen or the group NH,
n is 0 or 1 and
$R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, or of a salt of such a compound having at least one salt-forming group, for the manufacture of a medicament for treating tuberous sclerosis associated neoplasms or for the manufacture of a medicament for the prevention of neoplasms in patients suffering from tuberous sclerosis.

1-Methyl-1H-pyrrolyl is preferably 1-methyl-1H-pyrrol-2-yl or 1-methyl-1H-pyrrol-3-yl.

Amino- or amino-lower alkyl-substituted phenyl $R_1$ wherein the amino group in each case is free, alkylated or acylated is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$-$C_3$alkyl, such as especially methyl or ethyl.

1H-lndolyl bonded at a carbon atom of the five-membered ring is 1H-indol-2-yl or 1H-indol-3-yl.

Unsubstituted or lower alkyl-substituted pyridyl bonded at a ring carbon atom is lower alkyl-substituted or preferably unsubstituted 2-, 4- or preferably 3-pyridyl, for example 3-pyridyl, 2-methyl-3-pyridyl or 4-methyl-3-pyridyl. Pyridyl substituted at the nitrogen atom by oxygen is a radical derived from pyridine N-oxide, i.e. N-oxido-pyridyl.

Fluoro-substituted lower alkoxy is lower alkoxy carrying at least one, but preferably several, fluoro substituents, especially trifluoromethoxy or 1,1,2,2-tetrafluoro-ethoxy.

When X is oxo, thio, imino, N-lower alkyl-imino, hydrox-imino or O-lower alkyl-hydrox-imino, the group C=X is, in the above order, a radical C=O, C=S, C=N—H, C=N-lower alkyl, C=N—OH or C=N—O-lower alkyl, respectively. X is preferably oxo.

n is preferably 0, i.e. the group Y is not present.

Y, if present, is preferably the group NH.

The term "lower" within the scope of this text denotes radicals having up to and including 7, preferably up to and including 4 carbon atoms.

Lower alkyl $R_1$, $R_2$, $R_3$ and $R_9$ is preferably methyl or ethyl.

An aliphatic radical $R_{10}$ having at least 5 carbon atoms preferably has not more than 22 carbon atoms, generally not more than 10 carbon atoms, and is such a substituted or preferably unsubstituted aliphatic hydrocarbon radical, that is to say such a substituted or preferably unsubstituted alkynyl, alkenyl or preferably alkyl radical, such as $C_5$-$C_7$alkyl, for example n-pentyl. An aromatic radical $R_{10}$ has up to 20 carbon atoms and is unsubstituted or substituted, for example in each case unsubstituted or substituted naphthyl, such as especially 2-naphthyl, or preferably phenyl, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy. In an aromatic-aliphatic radical $R_{10}$ the aromatic moiety is as defined above and the aliphatic moiety is preferably lower alkyl, such as especially $C_1$-$C_2$alkyl, which is substituted or preferably unsubstituted, for example benzyl. A cycloaliphatic radical $R_{10}$ has especially up to 30, more especially up to 20, and most especially up to 10 carbon atoms, is mono- or poly-cyclic and is substituted or preferably unsubstituted, for example such a cycloalkyl radical, especially such a 5- or 6-membered cycloalkyl radical, such as preferably cyclohexyl. In a cycloaliphatic-aliphatic radical $R_{10}$ the cycloaliphatic moiety is as defined above and the aliphatic moiety is preferably lower alkyl, such as especially $C_1$-$C_2$alkyl, which is substituted or preferably unsubstituted. A heterocyclic radical $R_{10}$ contains especially up to 20 carbon atoms and is preferably a saturated or unsaturated monocyclic radical having 5 or 6 ring members and 1-3 hetero atoms which are preferably selected from nitrogen, oxygen and sulfur, especially, for example, thienyl or 2-, 3- or 4-pyridyl, or a bi- or tri-cyclic radical wherein, for example, one or two benzene radicals are annellated (fused) to the mentioned monocyclic radical. In a heterocyclic-aliphatic radical $R_{10}$ the heterocyclic moiety is as defined above and the aliphatic moiety is preferably lower alkyl, such as especially $C_1$-$C_2$alkyl, which is substituted or preferably unsubstituted.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl.

A substituted phenyl radical may carry up to 5 substituents, such as fluorine, but especially in the case of relatively large substituents is generally substituted by only from 1 to 3 substituents. Examples of substituted phenyl that may be given special mention are 4-chloro-phenyl, pentafluoro-phenyl, 2-carboxy-phenyl, 2-methoxy-phenyl, 4-fluoro-phenyl, 4-cyano-phenyl and 4-methyl-phenyl.

Salt-forming groups in a compound of formula I are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

COMPOUNDS of formula I having acidic groups, for example a free carboxy group in the radical $R_{10}$, may form metal or ammonium salts, such as alkali metal or alkaline earth metal salts, for example sodium, potassium, magnesium or calcium salts, or ammonium salts with ammonia or suitable organic amines, such as tertiary monoamines, for example triethyl-amine or tri-(2-hydroxyethyl)-amine, or heterocyclic bases, for example N-ethyl-piperidine or N,N'-dimethyl-piperazine.

COMPOUNDS of formula I having both acidic and basic groups can form internal salts.

Preference is given to COMPOUNDS of formula I wherein one or two of the radicals $R_4$, $R_5$, $R_6$, $R_7$ and $R_8$ are each nitro or a radical of formula II wherein
$R_9$ is hydrogen or lower alkyl,
X is oxo, thio, imino, N-lower alkyl-imino, hydroximino or O-lower alkyl-hydroximino,
Y is oxygen or the group NH,
n is 0 or 1 and
$R_{10}$ is an aliphatic radical having at least 5 carbon atoms or an aromatic, aromatic-aliphatic, cycloaliphatic, cycloaliphatic-aliphatic, heterocyclic or heterocyclic-aliphatic radical,
and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy,
and the remaining substituents are as defined above.

Preference is given especially to COMPOUNDS of formula I wherein
$R_1$ is pyridyl or N-oxido-pyridyl each of which is bonded at a carbon atom,
$R_2$ and $R_3$ are each hydrogen,
$R_4$ is hydrogen or lower alkyl,
$R_5$ is hydrogen, lower alkyl or trifluoromethyl,
$R_6$ is hydrogen,
$R_7$ is nitro, fluoro-substituted lower alkoxy or a radical of formula II wherein
$R_9$ is hydrogen,
X is oxo,
n is 0 and
$R_{10}$ is pyridyl bonded at a carbon atom, phenyl that is unsubstituted or substituted by halogen, cyano, lower alkoxy, carboxy, lower alkyl or by 4-methyl-piperazinyl-methyl, or $C_5$-$C_7$alkyl, thienyl, 2-naphthyl or cyclohexyl, and
$R_8$ is hydrogen.

Special preference is given to COMPOUNDS of formula I wherein at least one of the radicals $R_4$ and $R_8$ is lower alkyl, and the remaining substituents are as defined above.

Preference is given above all to COMPOUNDS of formula I wherein
$R_1$ is pyridyl bonded at a carbon atom,
$R_2$, $R_3$, $R_5$, $R_6$ and $R_8$ are each hydrogen,
$R_4$ is lower alkyl,
$R_7$ a radical of formula II wherein
$R_9$ is hydrogen,
X is oxo,
n is 0 and
$R_{10}$ is 4-methyl-piperazinyl-methyl.

Preference is given above all especially to the COMPOUND of formula I which is CGP 57148B {N-{5-[4-(4-methyl-piperazino-methyl)-benzoylamido]-2-methylphenyl}-4-(3-pyridyl)-2-pyrimidine-amine} or a pharmaceutically acceptable salt thereof. N-{5-[4-(4-methyl-piperazino-methyl)-benzoylamido]-2-methylphenyl}-4-(3-pyridyl)-2-pyrimidine-amine (hereinafter: "COMPOUND I" also known as "imatinib" [International Non-proprietary Name]) and the use thereof, are described in Example 21 of European patent application EP-A-0 564 409, which was published on 6 Oct. 1993, and in equivalent applications and patents in numerous other countries, e.g. in U.S. Pat. No. 5,521,184 and in Japanese patent 2706682. Another preference is given to the β-crystal form of 4-(4-methylpiperazin-1-ylmethyl)-N-[4-methyl-3-(4-pyridin-3yl)pyrimidin-2-ylamino)phenyl]-benzamide monomethanesulfonate as described in the European patent application No. 998 473 published on May 10, 2000. N-{5-[4-(4-methyl-piperazinomethyl)-benzoylamido]-2-methylphenyl}-4-(3-pyridyl)-2-pyrimidine-amine or a pharmaceutically acceptable salt will be referred herein as COMPOUND I; the β-crystal form of the mesylate salt of COMPOUND I will be referred as COMPOUND I mesylate.

The COMPOUNDS of formula I are generically and specifically disclosed in the patent applications EP 0 564 409 A1 and WO 99/03854, in particular in the compound claims and the final products of the working examples, the subject-matter of the final products, the pharmaceutical preparations and the claims are hereby incorporated into the present application by reference to these publications. Comprised are likewise the corresponding stereoisomers as well as the corresponding polymorphs, e.g. crystal modifications, which are disclosed therein. In EP 0 564 409 A1 the COMPOUNDS of formula I are described as PDGF receptor tyrosine kinase inhibitors useful for the treating cancer, thrombosis, psoriasis, fibrosis, dermatosclerosis and atherosclerosis.

Pharmaceutically acceptable salts of COMPOUNDS of formula I are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid.

The monomethanesulfonic acid addition salt of COMPOUND I (hereinafter "COMPOUND I mesylate") and crystal forms thereof, e.g. a preferred beta (β) crystal form thereof are described in PCT patent application WO99/03854 published on Jan. 28, 1999.

Very preferably a N-phenyl-2-pyrimidine-amine derivative of formula I is used in the form of its monomesylate salt.

For the purposes of isolation or purification, as well as in the case of compounds that are used further as intermediates, it is also possible to use pharmaceutically unacceptable salts. Only pharmaceutically acceptable, non-toxic salts are used for therapeutic purposes and those salts are therefore preferred.

Examples of suitable PDGF receptor tyrosine kinase inhibitors are COMPOUND I, RPR 101511A, SU 102, AG1296, AG1295, AG17, CT52923, RP-1776, KY11784, GFB-111, pyrrolo[3,4-c]-beta-carboline-diones, etc.

CT52923 (4-(6,7-dimethoxy-4-quinazolinyl)-N-(3,4-methylenedioxybenzyl)-1-piperazinethiocarboxamide) was described by Matsuno K, et al. (Synthesis and structure activity relationships of PDGF receptor phosphorylation inhibitor-1., in 18th Symposium on Medicinal Chemistry; 1998 Nov 25-27; Kyoto, Japan. The Pharmaceutical Society of Japan, Division of Medicinal Chemistry, Tokyo, Japan. Abstract 2-P-05).

KY11784 and RP-1776 novel cyclic peptides, were described by Toki S, Agatsuma T, et al (J Antibiot (Tokyo) 2001 May;54(5):405-14).

GFB-111 was described by Blaskovich M. A., et al. (Nat Biotechnol 2000 Oct;18(10):1065-70).

AG1296 and AG1295 were described by Kovalenko M, et al. (Cancer Res 1994 Dec 1;54(23):6106-14).

RPR 101511A was described by Bilder G, et al. (Circulation 1999 Jun 29;99(25):3292-9)

Pyrrolo[3,4-c]-beta-carboline-diones was described by Teller S, (Eur J Med Chem 2000 Apr;35(4):413-27).

AG17 (3,5-di-tert-butyl-4-hydroxybenzylidene-malononitrile or NSC 242557) was described by Gazit A et al.(Synthesis and biological activity of protein tyrosine kinase inhibitors. J Med Chem 1989;32:2344).

The present invention particularly concerns the use of PDGF receptor tyrosine kinase or bcr-abl tyrosine kinase inhibitors selected from COMPOUNDS of formula I, for the manufacture of a medicament for treating tuberous sclerosis associated neoplasms.

The present invention particularly concerns the use of PDGF receptor tyrosine kinase or bcr-abl tyrosine kinase inhibitors selected from COMPOUNDS of formula I, for the manufacture of a medicament for the prevention of neoplasms in patients suffering from tuberous sclerosis.

The present invention particularly concerns the use of COMPOUND I, which is a PDGF receptor tyrosine kinase inhibitor and a bcr-abl tyrosine kinase inhibitor.

By the term "tuberous sclerosis" the applicant means an autosomal dominant disorder characterized by the development of hamartomas and focal dysplasias in multiple organs including the brain (i.e. cortical and subcortical tubers, subependymal nodules, and giant cell astrocytomas, cerebral atrophy, cerebral infarct, cerebral aneurysm, arachnoid cyst), kidney (i.e. angiomyolipomas, cysts, carcinomas), skin (i.e. hypomelanotic macules, shagreen patches, facial angiofibromas, periungual fibromas), eye (i.e. retinal hamartomas), heart (i.e. rhabdomyomas), lungs (i.e. lymphangioleiomyomatosis), musculoskeletal manifestations (i.e. Sclerotic lesions, bone lucencies) and, to a lesser extent, other organs.

By the term "tuberous sclerosis associated neoplasms" the applicant means a tuberous sclerosis associated with abnormal tissues that grow by cellular proliferation more rapidly than normal and continue to grow after the stimuli that initiated the new growth cease. Neoplasms show partial or complete lack of structural organisation and functional coordination with the normal tissue, and usually form a distinct mass of tissue that may be either benign (benign tumor) or malignant (cancer). Preferred examples of tuberous sclerosis associated neoplasms are angiomyolipomas, e.g. renal angiomyolipomas, rhabdomyomas, lymphangioleiomyomatosis, subependymal giant cell astrocytomas or cutaneous neoplasms including fibrous plaques on the forehead and scalp, angiofibromas, e.g. facial angiofribromas, and periungual fibromas.

The term "treatment" as used herein means curative treatment and prophylactic treatment.

The term "curative" as used herein means efficacy in treating ongoing episodes of tuberous sclerosis associated neoplasms.

The term "prophylactic" means the prevention of the onset or recurrence of tuberous sclerosis associated neoplasms in patients suffering from tuberous sclerosis.

In accordance with the particular findings of the invention, the present invention also provides a method of treatment of a subject or patient that is a warm-blooded animal, including particularly a human, in which a therapeutically effective dose of a PDGF receptor tyrosine kinase or bcr-abl tyrosine kinase inhibitor or a pharmaceutically acceptable salt thereof is administered to such a warm-blooded animal, preferably a human, suffering from tuberous sclerosis associated neoplasms.

The invention relates also to a method for prophylactic treatment of neoplasms or prevention of neoplasms in a subject or patient that is a warm-blooded animal, including particularly a human, in which a therapeutically effective dose of a PDGF receptor tyrosine kinase or bcr-abl tyrosine kinase inhibitor or a pharmaceutically acceptable salt thereof is administered to such a warm-blooded animal, preferably a human, suffering from tuberous sclerosis.

Depending on species, age, individual condition, mode of administration, and the clinical picture in question, effective doses of COMPOUND I, e.g. COMPOUND I mesylate, for example daily doses of about 100-1000 mg, preferably 200-800 mg, e.g. 200 to 600 mg, or 400 mg, are administered to warm-blooded animals of about 70 kg bodyweight. For adult patients with unresectable tuberous sclerosis neoplasms, a starting daily dose corresponding to 400 mg of COMPOUND I free base can be used. For patients with an inadequate response after an assessment of response to therapy with 400 mg daily, dose escalation can be safely considered and patients may be treated as long as they benefit from treatment and in the absence of limiting toxicities.

Preferably COMPOUND I, e.g. COMPOUND I mesylate, is administered once daily for a period exceeding 3 months. The invention relates especially to such methods wherein a daily dose mesylate is administered corresponding to 100 to 1000 mg, especially 200-800 mg, preferably 200-600 mg or 400 mg of COMPOUND I free base.

It can be shown by established test models and especially those test model described herein that the PDGF receptor tyrosine kinase inhibitors, preferably COMPOUNDS of formula 1, e.g. COMPOUND I, or a pharmaceutically acceptable salt thereof, e.g. COMPOUND I mesylate, result in a more effective prevention of neoplasms and in an effective treatment of tuberous sclerosis associated neoplasms. The person skilled in the pertinent art is fully enabled to select a relevant test model to prove the hereinbefore and hereinafter indicated therapeutic indications and beneficial effects. The pharmacological activity may, for example, be demonstrated in a clinical study or in the test procedure as essentially described hereinafter.

Tumors often exhibit activation of specific tyrosine kinases, which may allow targeting of therapy through inhibition of tyrosine kinase signaling. It was hypothesized that tuberous sclerosis neoplasms may also show activation of a specific tyrosine kinase receptor, explaining in part the benign tissue specific neoplasms observed in tuberous sclerosis. Tuberous sclerosis associated cell lines were submitted to a battery of small molecular weight tyrosine kinase inhibitors. Tuberous sclerosis (TSC) model cells derived from tuberin heterozygous mice and from a human renal angiomyolipoma are highly sensitive to PDGF receptor antagonists and these cells express PDGFRβ. Expression of phosphorylated (active) PDGFRβ in vivo was detected using phospho-specific antibodies, as well as high level expression of the PDGFRβ signaling partner grb7 in human angiomyolipomas. Grb7 is highly expressed in angiomyolipomas, the most common tumor seen in TSC, but rarely in renal cell carcinoma. SV7tert human angiomyolipoma cells are particularly sensitive to COMPOUND I, and that COMPOUND I down regulates signaling molecules in human angiomyolipoma, including phosphorylation of Akt. In particular, the sensitivity to COMPOUND I occurred in a dose-dependent fashion. In addition, COMPOUND I inhibits PDGFRβ and bcr-abl tyrosine kinases. Thus, our results suggest that COMPOUND I might be useful in the treatment of neoplasms commonly seen in patients with TSC.

The following Examples illustrate the invention described above, but are not, however, intended to limit the scope of the invention in any way.

Methods

Derivation of Cell Lines

SV7tert (ATCC CRL 2461) is a cell line derived from a human angiomyolipoma through the sequential introduction of SV40 large T antigen and telomerase into primary human angiomyolipoma cells (Arbiser, J. L. et al. The generation and characterization of a cell line derived from a sporadic renal angiomyolipoma: use of telomerase to obtain stable populations of cells from benign neoplasms. *Am.J.Pathol.* 159, 483-491 (2001)). Angiomyolipomas are benign tumors of the kidney derived from putative perivascular epithelioid cells, that may undergo differentiation into cells with features of melanocytes, smooth muscle, and fat. Tsc2ang1 (ATCC CRL 2620) is a murine cell line derived from a cutaneous sarcoma arising in the extremity of a mouse heterozygous for tsc2. The sarcoma tissue was digested with collagenase and processed as described for SV7tert cells (Arbiser, J. L. et al.). Mice heterozygous for tsc2 develop cutaneous sarcomas at a frequency of approximately 10-15% (Onda, H., Lueck, A., Marks, P. W., Warren, H. B., & Kwiatkowski, D. J. Tsc2(+/−) mice develop tumors in multiple sites that express gelsolin and are influenced by genetic background. *J.Clin Invest* 104, 687-695 (1999)).

Tyrosine Kinase Inhibitor Studies

The following tyrosine kinase inhibitors were reconstituted as stock solutions in dimethyl sulfoxide (DMSO) immediately prior to use; AG9, AG17, AG18, AG30, AG82, AG99, AG112, AG370, AG490, AG879, AG957, AG1295, AG1296, AG1433, 2'thioadenosine, ST638, COMPOUND I, lavendustin C, oxindole 1, JAK3 inhibitors 1,2, and 3, as well as JAK3 inhibitor negative control. They can be obtained from Calbiochem (San Diego, Calif.). 10,000 cells per well in a 24 well dish were plated on day 1, and were treated with inhibitors in doses ranging from 0-2 μl (LaMontagne Jr K. R. Jr et al. Inhibition of MAP kinase kinase causes morphological reversion and dissociation between soft agar growth and in vivo tumorigenesis in angiosarcoma cells; *Am.J.Pathol.* 157,1937-1945 (2000)). Cells were counted 72 hours after treatment with inhibitors using a Coulter Counter (Coulter, Hialeah, Fla.).

Demonstration of PDGFRβ, Signal Transduction in SV7tert and tsc2ang1 Cells

Subconfluent cells in 6-hole wells were serum-starved over night and stimulated for 8 min with 50 ng/ml PDGF-BB (Peprotech EC, Ltd). The cells were lysed and used for immunoprecipitation with anti-PDGFRβ, antibodies (Santa Cruz Biotechnologies, Santa Cruz, Calif.). Immunoprecipitates were immobilized on protein A-Sepharose beads which were washed and boiled in SDS-sample buffer. The eluted material was separated on 10% SDS-polyacrylamide gels, transferred to filters and immunoblotted using anti-phosphotyrosine antibodies (4G10, Transduction Laboratories) or anti-PDGFRβ antibodies. Immunoreactive proteins were detected by enhanced chemoluminescence (ECL; Amersham Pharmacia Biotech). Western blot analysis of SV7tert and tsc2ang1 cells was also performed with a grb7 polyclonal Ab (Santa Cruz Biotechnologies, Santa Cruz, Calif.). Western blot analysis of SV7tert and tsc2ang1 cells was also performed with a grb7 polyclonal Ab (Santa Curx Biotechnologies, Santa Cruz, Calif.) and a polyclonal phosphoPLCgamma1 Ab (Biosource International, Camarillo, Calif.), following the instructions from the manufacturers.

Immunohistochemistry of Human Angiomyolipomas for Phosphorylated PDGFRβ and grb7

Sections of formalin-fixed, paraffin-embedded tissue (5 μm) were tested for the presence of immunohistochemically detectable antigen (phosphorylated PDGFRβ) with steam heat-induced antigen retrieval, polyclonal anti-phosphorylated PDGFRβ specific for phosphotyrosine 857 residue of PDGFRβ (Bernard, A. & Kazlauskas, A. Phosphospecific antibodies reveal temporal regulation of platelet- derived growth factor beta receptor (PCGFRβ) signaling. *Exp. Cell Res.* 253, 704-712 (1999)) (1/600), an avidin-biotinylated enzyme complex kit (LSAB, DAKO, Carpinteria, Calif.), and DAKO Autostainer. Sections were deparaffinized and rehydrated, then steamed in citrate buffer (pH=6) for 20 min and cooled for 5 min before immunostaining. All tissues were then exposed to 3% hydrogen peroxide for 5 min, primary antibody for 25 min, avidin-biotinylated enzyme complex for 25 min, diaminobenzidine as chromogen for 5 min and hematoxylin as counterstain for 1 min. These incubations were performed at room temperature; between incubations, sections were washed with buffer. For the two negative controls, primary antibody was replaced by buffer. Five-micron thick paraffin embedded tissue sections were deparaffinized and rehydrated. Antigen retrieval was performed in citrate buffer (pH6) using an electric pressure cooker at 120° C. for 5 min. The tissue was then exposed to 3% hydrogen peroxide for 5 min to quench endogenous tissue peroxidase. The tissue sections were incubated for 25 min with rabbit polyclonal anti-GRB 7 (1:40 dilution, Santa Cruz Biotechnology, Santa Cruz, Calif., USA) for 25 min. After washing unbound primary antibody, sections were treated with commercial biotinylated secondary anti-immunoglobulin followed by avidin coupled to biotinylated horseradish peroxidase, according to manufacturer's instructions (LSAB2 kit for mouse and rabbit primary antibodies, DAKO Corporation). Diaminobenzidine was used as the chromogenic peroxidase substrate for 5 min, and sections were counterstained with hematoxylin for 1 min after immunohistochemistry. These incubations were performed using automated immunostainer (DAKO, Carpinteria, Calif.). Specificity of the procedure was verified by negative control reactions with primary antibody replaced with buffer. Ten angiomyolipomas and ten renal cell carcinomas were examined.

Results

In order to determine whether human angiomyolipoma and tumors arising in mice heterozygous for tsc2 showed hypersensitivity to tyrosine kinase inhibitors, relevant human and mouse cell lines were exposed to a battery of tyrosine kinase inhibitors. These are tyrosine inhibitors which inhibit specific kinases, including JAK2 kinase, JAK3 kinase, platelet derived growth factor (PDGFR), epidermal growth factor receptor (EGFR), ERK½ inhibitor, p140 c-trk, p210 bcr-abl, p60 c-src, ErbB2, and vascular endothelial growth factor receptor 2 (VEGFR2/flk-1). Human SV7tert cells showed highest sensitivity to AG17 (Table 1), an inhibitor of PDGFR tyrosine kinase, and AG957, an inhibitor of p210 bcr-abl. Murine tsc2ang1 cells demonstrated hypersensitivity to AG17. Inhibitory compound AG17 is a substituted aromatic malononitriles. AG957 caused approximately 90% inhibition at 0.5 µg/ml (data not shown). AG1478 (Levitzki & Gazit. 1995. Science 267: 1782-1788; European Patent Application 0520722) and ST638 (Exp Cell Res 1989 Aug;183(2):335-42) are selective epidermal growth factor (EGF) receptor tyrosine kinase inhibitors and AG30 is a c-ErbB tyrosine kinase inhibitor. The c-ErbB tyrosine kinase receptor specific tyrphostin AG30 specifically blocked STAT5 activation (Cell Growth Differ 1997 May;8(5):481-93).

TABLE 1

Inhibition of proliferation of SV7tert and tsc2ang1 cells by tyrosine kinase inhibitors

| | Human SV7tert cells Compound | | | | | | | | | | Murine tsc2ang1 cells Compound | | | |
|---|---|---|---|---|---|---|---|---|---|---|---|---|---|---|
| | DMSO | | AG17 | | ST638 | | AG30 | | AG1478 | | DMSO | | AG17 | |
| CC in µg/ml | 10 | 20 | 10 | 20 | 10 | 20 | 10 | 20 | 10 | 20 | 10 | 20 | 10 | 20 |
| N (×100) | 252 | 248 | 23 | 22 | 250 | 205 | 250 | 270 | 251 | 210 | 185 | 185 | 23 | 23 |

(CC: concentration, N number of living cells after 72 h treatment).

AG17, a PDGFR kinase inhibitor, strongly inhibited both murine and human cell lines. In addition, COMPOUND I inhibits PDGFRβ tyrosine kinase in addition to bcr-abl and c-kit tyrosine kinase. The expression of functional PDGFRβ on both human SV7tert cells as well as on the murine tsc2ang1 cells was demonstrated by immunoblotting. Cells were treated with PDGF-BB or vehicle, and PDGFRβ was immunoprecipitated, followed by immunoblotting with anti-phosphotyrosine antibodies. We found that the expression level of PDGFRβ was slightly higher in tsc2ang1 cells compared with the SV7tert cells. In both cases, PDGF-BB treatment resulted in increased levels of phosphotyrosine-containing PDGFRβ. Furthermore, PDGF-BB treatment of tsc2ang1 cells resulted in activation of phospholipase C gamma (PLCγ), as an increase in phosphorylated PLCγ was noted after stimulation with PDGF-BB.

In order to determine whether our findings of PDGFRβ activation was truly associated with human angiomyolipomas in vivo, we stained authentic human angiomyolipoma tissue with an antibody specific for phosphorylated PDGFRβ. We observed strong staining for activated PDGFRβ, in the tumor sections, indicating that PDGF mediated signal transduction events occur in human angiomyolipomas in vivo. In addition, we examined human angiomyolipomas for the presence of grb7, a signaling partner of SV7tert, and found it to be expressed in 10/10 human angiomyolipomas, but in only 1/10 renal cell carcinomas. COMPOUND I was tested for its ability to inhibit the growth of SV7tert and tsc2ang1 in vitro. Human SV7tert angiomyolipoma cells demonstrated increased sensitivity to COMPOUND I compared to murine tsc2ang1, and this sensitivity occurred in a dose-dependent fashion. Treatment of SV7tert cells with COMPOUND I resulted in downregulation of Akt phosphorylation after 24 hours of treatment, suggesting that COMPOUND I may inhibit PDGFRβ, stimulation of P13 kinase-signaling (see Table 2).

TABLE 2

Inhibition of SV7tert cells by COMPOUND I.

| | concentration of COMPOUND I | | | |
|---|---|---|---|---|
| | Control | 2 µg/ml | 5 µg/ml | 10 µg/ml |
| No. of Cells after 72 hours | 22450 | 16500 | 10000 | 6500 |

Tuberous sclerosis model cells (associated with neoplasms) derived from tuberin heterozygous mice and from a human renal angiomyolipoma are highly sensitive to PDGF receptor antagonists and these cells express PDGFRβ.

EXAMPLE 2

Capsules With 4-[(4-methyl-1-piperazin-1-ylm-ethyl)-N-[4-methyl-3-[[4-(3-pyridinyl)-2-pyrimidi-nyl]amino]phenyl]benzamide methanesulfonate, or its β-crystal form Capsules containing 119.5 mg of the compound named in the title (=COMPOUND I mesylate) corresponding to 100 mg of COMPOUND I (free base) as active substance are prepared in the following composition:

| | |
|---|---|
| COMPOUND I mesylate | 119.5 mg |
| Cellulose MK GR | 92 mg |
| Crospovidone XL | 15 mg |
| Aerosil 200 | 2 mg |
| Magnesium stearate | 1.5 mg |
| | 230 mg |

The capsules are prepared by mixing the components and filling the mixture into hard gelatin capsules, size 1.

EXAMPLE 3

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, b-crystal form Capsules containing 119.5 mg of SALT I corresponding to 100 mg of COMPOUND I (free base) as active substance are prepared in the following composition:

| | |
|---|---|
| Active substance | 119.5 mg |
| Avicel | 200 mg |
| PVPPXL | 15 mg |
| Aerosil | 2 mg |
| Magnesium stearate | 1.5 mg |
| | 338.0 mg |

The capsules are prepared by mixing the components and filling the mixture into hard gelatin capsules, size 1.

What is claimed is:

1. A method of treating a patient suffering from tuberous sclerosis associated neoplasms comprising administering to a subject in need thereof an effective amount of N-{5-[4-(4-methyl-piperazino-methyl)-benzoylamido]-2-methylphenyl}-4-(3-pyridyl)-2-pyrimidine-amine, or a pharmaceutically acceptable salt thereof.

2. The method according to claim 1, wherein the pharmaceutically acceptable salt is a monomesylate salt.

3. The method according to claim 1, wherein a monomethanesulfonate salt of N-{5-[4(4-methyl-piperazino-methyl)-benzoylamido]-2-methylphenyl}-4-(3-pyridyl)-2-pyrimidine-amine is administered at a daily dose corresponding to 100 to 1000 mg of N-{5-[4-(4-methyl-piperazino-methyl)-benzoylamido]-2-methylphenyl}-4-(3-pyridyl)-2-pyrimidine-amine free base.

4. The method according to claim 1 wherein the tuberous associated neoplasm is selected from angiomyolipomas, rhabdomyomas, lymphangioleiomyomatosis, subependymal giant cell astrocytomas, angiofibromas and periungual fibromas.

5. The method according to claim 1 wherein the tuberous sclerosis associated neoplasm is an angiomyolipoma.

* * * * *